Figure 1:
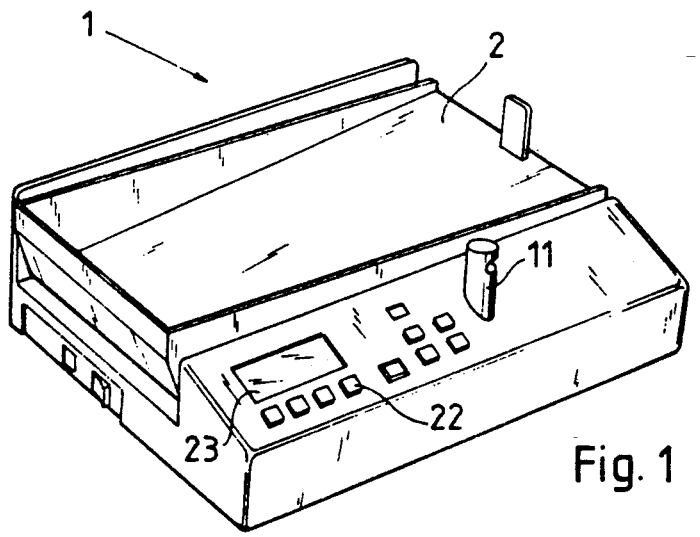

United States Patent [19]
Kögel

[11] Patent Number: 5,147,330
[45] Date of Patent: Sep. 15, 1992

[54] BLOOD CRADLE

[75] Inventor: Arne Kögel, Sollentuna, Sweden

[73] Assignee: Ljungberg & Kögel, Sollentuna, Sweden

[21] Appl. No.: 598,073

[22] Filed: Oct. 16, 1990

[30] Foreign Application Priority Data

Oct. 18, 1989 [SE] Sweden ............................. 8903440

[51] Int. Cl.$^5$ ............................................. A61M 5/05
[52] U.S. Cl. .................................. 604/245; 604/403; 604/408; 604/903
[58] Field of Search ............... 604/245, 250, 903, 403, 604/408–410; 177/118, 245

[56] References Cited

U.S. PATENT DOCUMENTS

| | | | |
|---|---|---|---|
| 3,698,494 | 10/1972 | Gaudin | 177/118 |
| 3,960,224 | 6/1976 | Silvers | 604/245 |
| 4,267,837 | 5/1981 | Purdy et al. | 604/245 X |
| 4,460,358 | 7/1984 | Somerville et al. | 604/245 X |
| 4,559,045 | 12/1985 | Danby et al. | 604/250 |
| 4,585,441 | 4/1906 | Archibald | 604/245 |
| 4,585,442 | 4/1986 | Mannes | 604/250 |
| 4,923,449 | 5/1990 | Toya et al. | 604/245 |
| 5,010,968 | 4/1991 | Barrow | 604/250 X |

*Primary Examiner*—Robert A. Hafer
*Assistant Examiner*—Kerry Owens
*Attorney, Agent, or Firm*—Nies, Kurz, Bergert & Tamburro

[57] ABSTRACT

A cradle for use in blood donating processes comprises surface (2) which is intended to support a blood-collecting bag and to-be rocked reciprocatingly on an axle (4) which extends perpendicularly to the surface, by means of a crank (5, 7). The cradle is provided with a weight measuring device (8) which functions to measure the quantity of blood that has flowed into the bag, and is also fitted with a clamping device (11) which functions to clamp-on or squeeze the hose such as to prevent blood from flowing therein and which is operable electromagnetically. The cradle is further provided with a control circuit (21) which is constructed to control at least the clamping device (11). The cradle is characterized in that the control circuit (21) is constructed so that, upon receipt of a given signal from the operator, it will cause the clamping device (11) to clamp-on the hose, and will cause the clamping device (11) to release the hose in response to a given start signal from the operator; and in that the control circuit (21) is constructed to cause the clamping device to alternately clamp-on the hose and release the hose in a manner such as to release a small quantity of blood at a time when a given, predetermined amount of blood remains to be taken from the donor; and in that the control circuit is constructed in a known manner to cause the clamping device to clamp-on the hose when a predetermined amount of blood has flowed into the blood bag.

3 Claims, 1 Drawing Sheet

U.S. Patent  Sep. 15, 1992  5,147,330

BLOOD CRADLE

The present invention relates to a cradle for use when taking blood from a blood donor and being of the kind used to rock a blood collecting bag backwards and forwards in order to mix an anticoagulant with the blood that is drained from the vein of a blood donor into the bag.

The task of taking blood from a donor requires many manual operations on the part of the person taking the blood. The blood collecting bags which are normally used, and also the hose connected to the bags and intended to be fitted to a cannula are prefilled with an anticoagulant.

Various cradles of this kind are known to the art. For instance, cradles are known which include a bag-carrying surface which is caused to rock forwards and backwards with the aid of a crank device which rotates about an axle which extends perpendicularly to the bag-carrying surface. It is also known to provide such cradles with a weight-measuring device which functions to measure the amount of blood that has flowed into the bag. It is also known to provide such cradles with means which function to produce an alarm signal when blood flows too quickly or too slowly into the bag.

It is also known to provide such cradles with clamping devices which are intended to clamp or squeeze the hose subsequent to a predetermined weight of blood entering the bag. This clamping device includes a cylindrical member which moves in a cylindrical tube. The hose can be introduced through an aperture provided in the tube wall. The cylindrical member is moved within the tube by means of an electromagnet or solenoid. When a hose is introduced into the aperture and the cylindrical member is moved towards said aperture, the hose is squeezed so as to interrupt the flow of blood therethrough.

As beforementioned, the person taking blood from a blood donor is required to carry out a number of operations. One operation involves applying a clamp to the hose prior to connecting the hose to a cannula and removing the protective sleeve therefrom. If a hose clamp has not been applied, when the protective sleeve is removed the anticoagulant will flow down into the bag, while drawing air into the hose at the same time. This air may well be contaminated with bacteria and virus. The cannula is inserted into a vein of the donor with the clamp applied to the hose, whereafter the hose clamp is removed and blood is taken from the vein.

In certain applications it is extremely important that the bag contains a precise quantity of blood. The clamping device of known blood cradles is not constructed to cut-off the flow of blood into the bag with sufficient precision.

It is also important that the wall of the hose is fused-off so as to seal the hose before the blood is able to coagulate in the hose. Known cradles of this kind are constructed to produce an acoustic signal and to squeeze the hose together with the aid of the clamping device when a predetermined quantity of blood has been obtained. The blood then coagulates quite quickly in the hose, and consequently it is necessary for the person taking blood from the donor to remove the cannula and fuse-off and thus seal the hose relatively quickly.

The aforesaid manual operations are greatly facilitated by means of the present invention.

The present invention thus relates to a cradle of the kind which includes a bag-carrying surface which is intended to be rocked reciprocatingly about an axle which extends perpendicularly to said surface, by means of a crank device or the like, said cradle being provided with a weight measuring device which functions to measure the quantity of blood that has flown into the blood bag, and wherein the cradle is provided with a clamping device which functions to squeeze said hose so as to prevent blood from flowing therein, said clamping device being electromagnetically operable, and wherein the cradle is provided with a control circuit which functions to at least control said clamping device, said cradle being characterized in that said control circuit is constructed, upon receipt of a signal from the operator, to cause the clamping device to clamp around the hose, and upon receipt of a given start signal from the operator to cause the clamping device to release the hose; and in that said control circuit is constructed to cause the clamping device to clamp the hose and then to release the hose so as thereby to allow a small quantity of blood to pass on each occasion when a given predetermined quantity of blood remains to be takenfrom the donor; and in that the control circuit is constructed in a known manner to cause the clamping device to clamp the hose when a predetermined quantity of blood has flown into the blood bag.

The invention will now be described in more detail with reference to an exemplifying embodiment thereof illustrated in the accompanying drawing, in which FIG. 1 is a perspective view of a cradle for use in blood donating processes.

Figure 2:
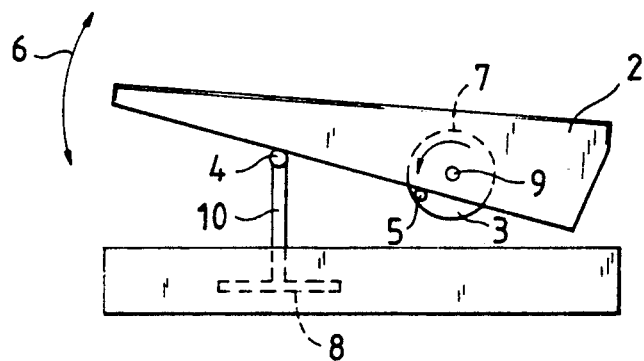
Figure 3:
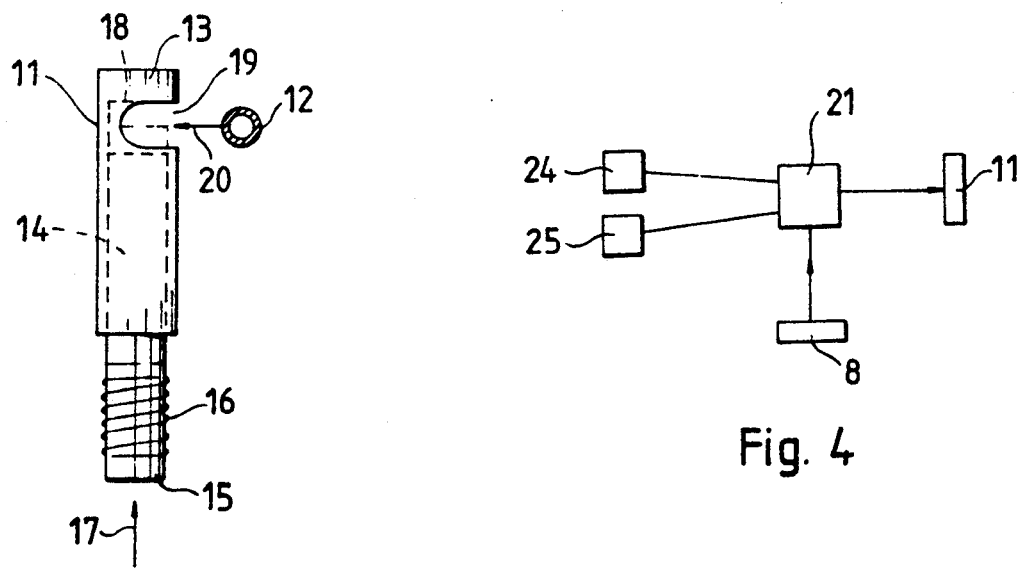
Figure 4:
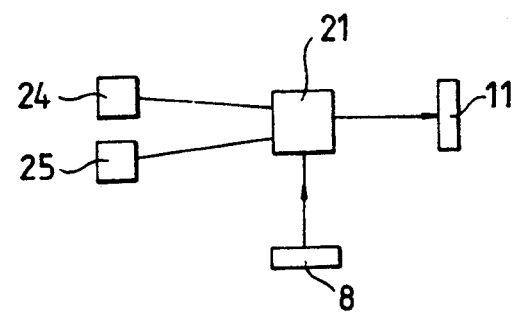

FIG. 2 is a diagramatic side elevation view which illustrates part of the cradle trayrocking mechanism, FIG. 3 is an enlarged view of a hose clamping device, and FIG. 4 is a block schematic of the controls and control circuit for the cradle apparatus of FIG. 1.

FIG. 1 illustrates a cradle 1 which includes a tray or carrier surface 2 for supporting a blood collecting bag, which is placed on said surface. The surface 2 is intended to be rocked reciprocatingly about an axle 4 which extends perpendicularly to said surface, as shown by the arrow 6, by means of a crank 3 or the like, see FIG. 2. The crank may comprise a disc 7 rotatably mounted on a shaft 9 and provided with a wheel 5 which runs on the underside of said carrier surface.

The cradle 1 is provided with a weight measuring device 8 which functions to weigh the amount of blood that has flowed into a blood collecting bag supported on the carrier 2. The carrier 2 is supported by a rod 10, which in turn is supported by the weight measuring device 8. The weight measuring device conveniently comprises a plate fitted with a strain gauge. The device 8 is constructed to produce an electric signal which constitutes a measurement of the detected weight.

The cradle 1 is also provided with a clamping device 11 which is intended to squeeze or clamp together a hose 12 extending between the bag and a cannula intended for insertion into a vein of a blood donor. In its activated position, the clamping device clamps the hose so as to prevent blood from flowing therethrough.

The clamping device is of a known kind and is actuable electromagnetically. According to one embodiment, see FIG. 3, the clamping device includes a tube 13 in which a rod 14 moves. The bottom end of the rod 14 is connected to an iron core 15 which is intended to move within an electric coil 16. When the coil is supplied with direct current in one direction, the core 15 is moved upwards, as indicated by the arrow 17, therewith moving the rod upwards into engagement with a stop 18. The tube 13 is provided with an aperture 19 through which a hose can be introduced, as illustrated by the arrow 20. The hose 12 is shown in cross-section in FIG. 3. When a hose is inserted into the aperture and the rod 14 is moved upwards, the hose is clamped so as to prevent blood from flowing in the hose.

The cradle 1 is also provided with a control circuit 21 which is constructed to control at least the clamping device. The control circuit will suitably include a microprocessor provided with conventional input and output circuits.

Mounted on the cradle is a panel which includes a number of electrical switches or buttons 22 and a display 23. The cradle can be started and stopped with the aid of the switches, via the control circuit. The amount of blood to be taken from a donor can also be set on the panel display 23 by buttons 22. The display enables the amount of blood taken from the donor at any one period time to be read-off, and also the time during which blood has been taken from the donor.

Two switches or buttons are of particular interest to the present invention, namely a switch 24 for manouvering the clamping device and a switch 25 for initiating the blood taking operation. These switches are connected to the control circuit 21, see FIG. 4. Also connected to the control circuit are the weight measuring device 8 and the clamping device 11.

According to the present invention, the control circuit 21 is constructed to activate the clamping device upon receipt of a given signal from the operator, such as to clamp the hose, and to activate the clamping device upon receipt of a given start signal from the operator, so as to release the hose.

This is a facility which is used when commencing to take blood from a donor. When blood is to be taken from a donor, a blood collecting bag is placed on the tray or carrier 2 and the hose 11 is introduced into the aperture 19. The operator then presses the button or switch 24, wherewith the control circuit causes the clamping device to clamp on the hose. The operator then removes the protective sleeve from the cannula and inserts the cannula into a vein of the donor. Because the clamping device clamps on the hose, liquid in the hose is unable to flow when the protective sleeve is removed from the cannula, and hence no air will enter the hose.

Subsequent to inserting the cannula, the operator presses the start button or switch 25 to produce said start signal, wherewith the control circuit causes the clamping device to release its pressure on the hose so that blood can be taken from the donor. The cradle 2 will then begin to rock, the time count commences and the weight measuring device is tared and begins to emit a continuous measuring signal.

The control circuit 21 is also constructed to cause the clamping device 11 to alternately clamp and release the hose, such as to allow a small quantity of blood to flow through the hose on each occasion, when a given, predetermined amount of blood remains to be taken from the donor. The control circuit is thus constructed to compare the amount of blood taken from the donor with the preset amount.

Furthermore, the control circuit 21 is constructed in a known manner to cause the clamping device 11 to clamp the hose when said predetermined amount of blood has flowed into the blood collecting bag.

According to one preferred embodiment of the invention, the control circuit 21 is constructed to cause the clamping device 11 to alternately clamp and release the hose, as beforementioned, when an amount of from 5–25 ml of blood remains to be taken from the donor, preferably about 10 ml. This enables the blood taken from a donor to be measured very precisely, as opposed to the case with known cradles of this kind.

In accordance with another preferred embodiment of the invention, the control circuit 21 is constructed such that subsequent to having caused the clamping device 11 to clamp on the hose when the predetermined quantity of blood has been obtained, it causes the clamping device 11 to release the hose and thereafter again to clamp-on the hose, so as to release a small quantity of blood through the hose. This prevents coagulation of the blood in the hose.

It will be evident from the aforegoing that the present invention avoids the drawbacks associated with known blood cradles.

The invention has been described in the aforegoing with reference to an exemplifying embodiment thereof. It will be obvious, however, that the cradle itself, and also the structural design of the clamping device can be varied without changing the aforedescribed operator function.

The present invention shall not therefore be considered to be limited to the illustrated embodiment, since modifications can be made within the scope of the following claims.

I claim:

1. A blood-collecting bag cradle comprising a bag carrier, with a support surface, adapted to support a blood-collecting bag, means including an axle connected to and extending under and essentially parallel with said surface, and a crank offset from and parallel with said axle and engaging said carrier for reciprocatingly rocking said carrier on said axle, said cradle also being provided with a weight measuring device connected to said carrier to measure the quantity of blood that has flowed into the bag, said cradle also being provided with a clamping device adapted to receive a part of a hose connected to the blood-collecting bag and operable to clamp and unclamp the hose to respectively prevent and permit flow of blood therethrough and electromagnetic power means to operate said clamping device, and said cradle including a control circuit means connected to said power means to control at least the clamping device, said control circuit means being so constructed and connected to said clamping device so that, upon receipt of a first signal from an operator, the control circuit means will operate the power means for said clamping device to clamp the hose, and, in response to a second, start, signal from an operator, will operate the power means for said clamping device to unclamp said hose; and wherein said control circuit means includes first control means responsive to said weight measuring device to operate the clamping device to alternately positively clamp the hose and to unclamp said hose, by operating said electromagnetic power means, so as to permit passage of a small quantity of blood at a time through said hose when a given amount of blood remains to be taken from the donor; and wherein the control circuit means has additional means also responsive to said weight measuring device to operate said power means to cause the clamping device to clamp the hose when a predetermined total amount of blood has flowed into the blood-collecting bag.

2. A blood-collecting bag cradle according to claim 1, wherein the first means in said control circuit means responsive to said weight measuring device senses when all but 5–25 ml. of the predetermined total amount of blood has been taken and actuates said power means for said control circuit means to cause said clamping device to alternately clamp the hose and unclamp the hose, to slow down the flow of blood.

3. A blood-collecting bag cradle according to claim 1, wherein said additional means responsive to said weight measuring device will supplementarily actuate said control circuit means, subsequent to having caused the clamping device to clamp the hose when the predetermined total amount of blood has been obtained, to again operate said clamping device to unclamp the hose and then to immediately again clamp the hose, thereby to allow a small amount of blood to pass through the hose into the bag.

* * * * *